United States Patent [19]

Thiel et al.

[11] 3,946,077

[45] Mar. 23, 1976

[54] PROCESS FOR OXIDATING HYDROCARBONS

[75] Inventors: Reinhard Thiel; Heinz Jörg Rosenbaum; Karl Heinz Heller, all of Krefeld, Germany

[73] Assignee: Bayer Aktiengesellschaft, Leverkusen, Germany

[22] Filed: Feb. 4, 1974

[21] Appl. No.: 439,689

[30] Foreign Application Priority Data

Mar. 28, 1973 Germany............................ 2315350

[52] U.S. Cl.... 260/586 AB; 260/586 P; 260/597 R; 260/617 R; 260/617 M; 260/631 R; 260/632 C; 260/632 CB; 260/631 B
[51] Int. Cl.² .................. C07C 27/12; C07C 27/16; C07C 29/00; C07C 45/02
[58] Field of Search ........ 260/586 B, 631 B, 462 A, 260/586 P, 586 AB, 631 R, 617 R, 617 M, 632 C, 632 CB, 597 R

[56] References Cited
UNITED STATES PATENTS 3,232,704  2/1966  Helbig et al...................... 260/586 B
3,243,449  3/1966  Winnick........................... 260/631 B
3,316,302  4/1967  Steeman et al.................. 260/586 B
3,796,761  3/1974  Marcell et al..................... 260/462 A Primary Examiner—Norman Morgenstern
Attorney, Agent, or Firm—Burgess, Dinklage & Sprung

[57] ABSTRACT

Hydrocarbons containing from 4 to 20 carbon atoms are oxidized with a gas containing molecular oxygen in the presence of a catalyst and/or auxiliary agents. The resulting reaction mixture is saponified with an aqueous alkaline solution and the resulting alkaline solution containing organic impurities is subjected to liquid phase oxidation with a gas containing molecular oxygen in at least a stoichiometric quantity sufficient for completely burning the organic ingredients, the oxidation taking place in a reaction zone heated to at least 200°C under a pressure sufficient to keep at least some of the water in the liquid phase. The alkali carbonate/bicarbonate solution formed is recycled to the hydrolysis stage.

15 Claims, 2 Drawing Figures

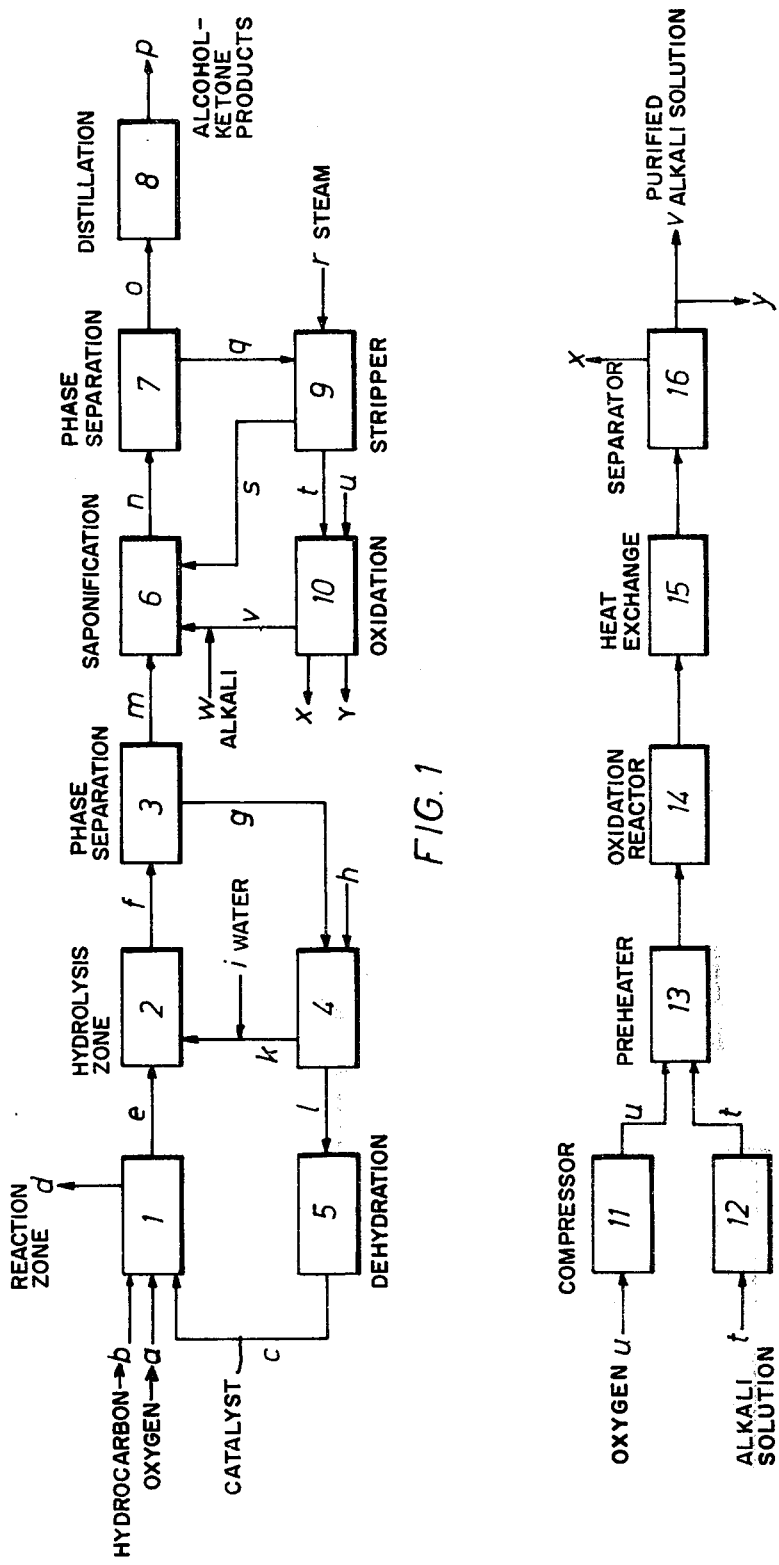

PROCESS FOR OXIDATING HYDROCARBONS

BACKGROUND

This invention relates to a process for the oxidation of hydrocarbons with gases containing molecular oxygen to form the corresonding alcohol-ketone mixtures. More particularly, the invention relates to a process in which the recovery and reuse of the saponification liquor used to purify the reaction mixture is effected by oxidation of the organic by-products dissolved in the saponification liquor.

Hydrocarbons can be oxidised using gases containing molecular oxygen. Oxidation into alcohols is of considerable commercial significance, being carried out in the presence of catalysts or other auxiliary substances in order to increase selectivity.

Typical oxidation catalysts are described for example in DOS No. 2.028.166, and are inorganic and organic compounds of transition metals, preferably cobalt and manganese.

Reference is made here by way of example to cobalt naphthenates, cobalt oleate, cobalt stearate and cobalt ethyl hexanoate and to te cobalt salt of a stoichiometric mixture of the monoester and the diester of iso-tridecanol with orthophosphoric acid.

U.S. Pat. No. 3,243,449 describes boron compounds as esterification component for the alcohol formed during the oxidation process. The compounds are used in at least stoichiometric quantities, based on the alcohol content of the oxidation mixture.

Typical boron compounds used in oxidation processes of this kind include boric acids, for example orthoboric acid and metabroic acid and boric acid esters such as the monoester of metaboric acid and the alcohol of the hydrocarbon to be oxidised, for example cyclohexyl metaborate when cyclohexane is the starting compound, and boric acid anhydrides such as, for example, $B_2O_3$ and $B_4O_5$. Mixtures of these boron compounds can also be used.

The reaction mixture is washed with water or hydrolysed with water in order to separate off the water-soluble secondary products formed by the oxidation of the hydrocarbons and, if necessary, the boron compounds used. In industrial processes, the aqueous phase is generally cycled; a component stream of the aqueous solution is removed from the circuit to recover the boron compounds used and to work up the secondary products present therein.

In addition to the required alcohol-ketone mixture, the organic phase left after washing with water contains unreacted hydrocarbon, other monoalcohols and dialcohols, aldehydes and ketones, esters of mono-, di- and hydroxycarboxylic acids and also residues of unesterified carboxylic acids. These mixtures are normally washed with alkalis in order to saponify the esters and to separate off both the residual and the liberated carboxylic acids. The alkaline wash is carried out for example with aqueous sodium hydroxide or a soda solution (DOS No. 2,118,279) in a concentration of from 1.5 to 14%, preferably from 3 to 10% by weight, of sodium ions.

In addition to small quantities of free alkali, the saponification liquor which accumulates during this stage of the process, irrespective of the particular oxidation process applied, contains the alkali salts of the carboxylic acids formed as secondary products together with other products of the oxidation process which, although not acidic, are soluble in aqueous, dilute liquor, such as for example monoalcohols and dialcohols. In order to recover the valuable monoalcohols, the saponification liquor is distilled in the first stage or stripped by blowing in steam. The end liquor left containing in addition to the alkali, large quantities of organic secondary products, is removed from the process. In industrial process, this end liquor generally contains from 5 to 15 % by weight of organically combined carbon or about 30 to 120 kg of C/t of alcohol-ketone mixture produced.

The organic ingredients have to be eliminated in order to protect the environment from pollution. The methods hitherto proposed for this purpose are unsatisfactory. Biological purification involves extremely high costs on account of the large quantities of dissolved organic ingredients. In addition, it is attended by the disadvantage that all the alkali enters the main drainage system with the effluent Attempts to burn the saponification liquor have revealed significant technical difficulties. The alkaline melt residue which assumulates in the combustion furnace has a pronounced decomposition effect on all lining materials. The same applies to a greater extent as regards residues containing alkali borate which inevitably accumulate during the combustion of hydrolysis liquors from oxidation processes carried out in the presence of boron compounds. This results in inadequate running times for industrial combustion installations.

A process has now been found by means of which alkalis can be recovered and, at the same time, the organic ingredients of the described saponification liquor eliminated. Accordingly, the invention relates to a process for the oxidation of hydrocarbons during which the hydrolysis liquor is purified by wet oxidation of the organic impurities into essentially carbon dioxide and water by treatment with gases containing molecular oxygen at elevated temperatures and under elevated pressure. The alkali carbonate/bicarbonate liquor formed is returned to the process as saponification liquor.

SUMMARY

Accordingly, the invention provides a process; for the oxidation of hydrocarbons having 4 to 20 carbon atoms with gases containing molecular oxygen in the presence of catalysts or auxiliary agents, for example, boron compounds, in which secondary products and, if necessary, auxiliary substances are separated off in an intermediate stage comprising a water wash or hydrolisis, and the organic reaction mixture saponified with an aqueous, alkaline solution, characterised by the fact that the aqueous, spent alkali salt solution which accumulates containing organic impurities, is subjected to liquid-phase oxidation with gases containing molecular oxygen in at least stoichiometric quantities sufficient for complete combustion of the organic impurities in a reaction zone heated to a temperature of at least 200°C under a pressure which is sufficient to keep at least some of the water in the liquid phase, and the resulting alkali carbonate/bicarbonate solution is returned to the saponification stage.

DESCRIPTION

This oxidation process can be carried out with saturated, linear, branched or cyclic hydrocarbons having 4 to 20 carbon atoms per molecule, for example cyclopentane, cyclohexane, methylcyclohexane, cycloheptane, dimethylcyclohexane, cyclododecane, n-butane, n-pentane, n-hexane, $C_{12} - C_{14}$ - petroleum naphthane, octadecane, nonadecane and eicosane. Hydrocarbons having 5 to 12 carbon atoms can be oxidised with advantage, cyclohexane and cyclododecane with particular advantage, into the corresponding alcohol/ketone mixture by the process according to the invention. The starting material does not have to be completely free from unsaturated substance (for example cyclohexane in the case of cyclohexane) in order to be suitable for use in the process according to the invention, the only requirement in this respect being that more than 95 mol % of the starting material should consist of saturated hydrocarbons.

In the context of the present invention, gases containing molecular oxygen are, for example, pure oxygen, oxygen-air mixtures, an oxygen-nitrogen (or other inert gases) mixture, air or air diluted with nitrogen, $CO_2$ or water vapour.

The spent alkaline solution containing the alkali salts of mono-, di- and hydroxy-carboxylic acids and alcohols as impurities had not been expected to lend itself to purification by liquid-phase oxidation to such an extent that the treated liquor can be completely recirculated and, hence, the alkali used recovered in the form of an alkali carbonate/bicarbonate solution. Another surprising aspect was that the high temperatures used did not give rise to any resin-forming and sludge-forming reactions which would have severely complicated simple recirculation of the liquor.

DESCRIPTION OF THE DRAWING

The process according to the invention is diagrammatically illustrated in FIGS. 1 and 2 of the accompanying drawings with reference, by way of example, to the oxidation of cyclohexane with air in the presence of metaboric acid to form a mixture of cyclohexanol and cyclohexanone.

Cyclohexane, air and metaboric acid are delivered to the reaction zone 1 through the pipes $a$, $b$ and $c$. Low-oxygen waste gas is discharged from the reaction zone through pipe $d$. The reaction mixture flows through pipe $e$ into the hydrolysis zone 2 where it is contacted with an aqueous stream $k$.

The boric acid esters formed in the reaction zone 1 decompose into the corresponding alcohol and boric acid. After phase separation in zone 3, orthoboric acid is recovered for the aqueous stream $g$ by low-temperature crystallisation in vacuo and centrifuging the crystal sludge formed in 4, being returned to the reaction in the form of metaboric acid through $c$ after dehydration in the dehydrater 5. Fresh orthoboric acid is introduced through pipe $h$ after dissolution in water. The mother liquor accumulating during crystallisation and the condensed crystal vapours are delivered to the hydrolysis zone 2 through the pipe $k$ and fresh water through the pipe $i$. The organic phase separated in zone 3 consists of unreacted cyclohexane, cyclohexynol, cyclohexanone, secondary products such as cyclohexyl esters of mono-, di- and hydroxycarboxylic acids having 1 to 6 carbon atoms, other alcohols such as butanol, pentanol, cyclohexane-1,2- and -1,3-diol and of small quantities of water and incompletely extracted boric acid. It is contacted with the aqueous liquor stream $v$ in the saponification stage 6. The esters are saponified and the water-soluble secondary products extracted. After phase separation in the separation vessel 7, the organic phase is worked up in the distillation stage 8 into a mixture of cyclohexanol and cyclohexanone. Valuable cyclohexanol and other water-vapour-volatile secondary products are removed from the aqueous alkaline phase in the liquor stripper 9 by blowing in stream ($r$). The vapours which accumulate are condensed. The resulting condensate is returned to the saponification stage ($s$). The stripped alkali salt solution is delivered to the wet-oxidation stage 10 where it is contacted with air, introduced through pipe $u$, at an elevated temperature and pressure. As a result, the organic ingredients are oxidised essentially into $CO_2$ and $H_2O$. The waste gases, consisted predominently of $N_2$ and $CO_2$, are run off through the pipe X. The alkaline solution thus purified is returned through $v$ to the saponification stage 6. Fresh liquor is introduced through the pipe $w$. Sodium tetraborate slowly accumulates in the sofonification liquor circuit. Since it is not troublesome either during wet oxidation or during saponification, its concentration can be allowed to rise until it approaches the solubility limit. Any further increase in the concentration of sodium tetraborate is prevented by removing a small component stream $y$ of the alkaline solution.

The wet-oxidation stage carried out in the zone 10 is illustrated in FIG. 2 for continuous working. However, the process can also be carried out in batches. Oxygen-containing gas, for example pure oxygen, air or an oxygen-containing fraction emanating from the air-separation, is compressed to the required reaction pressure by means of the compressor 11 and, in the same way as the stream $t$ of alkali salt solution delivered by the high pressure pump 12, passes through a preheater 13 into the high-pressure reactor 14. After passing through the reaction zone, the gas-liquid mixture is cooled in a heat exchanger 15 and separated in the separator 16 into waste gas (stream $x$) and liquor. The purified alkaline liquor is returned to the saponification stage through pipe $v$. A component stream $y$ may optionally be removed as effluent.

The process stages illustrated in FIG. 2 are representative of a number of known possible variations. For example, the reaction gas and alkaline solution can be preheated either together or separately, for which purpose the reaction mixture issuing from the reactor can, of course, be used as heating medium. The input then serves as coolant for the output. To initiate the reaction and to start up the system, the preheater must also be designed to be heated by another heating medium. In addition, the heat of reaction has to be dissipated in another, following condenser. Heat available for heating other systems is obtained in this way.

There are also numerous variants for the reaction zone 14. It can be operated in parallel current or in countercurrent either in one or in several stages. The reactor(s) can be provided with a pressure-tight stirrer and/or can contain other attachments suitable for the favourable distribution of gas. The reaction conditions (temperature, pressure and residence time) can also differ from one reaction stage to the other. For example, it is advisable to operate the final stage through which the liquor passes at a higher temperature and/or with a longer residence time if the reaction of the organic ingredients to form $CO_2$ and $H_2O$ is required to be particularly complete.

To conserve energy, the highly compressed waste gas ($x$) can be passed for example through a turbine which in turn transfers the energy to the compressor 11.

The reaction conditions for the process according to the invention are variable within wide limits. The reaction temperature can be in the range from 200° to 370°C and is preferably in the range from 270° to 350°C. The reaction pressure should be higher than the water vapour pressure at the particular reaction temperature. Accordingly, the pressure can vary from 20 to 220 atms. and preferably from 60 to 200 atms. In addition, the quantity of water in the liquid phase should be at least such that the solubility of the ingredients of the alkaline liquor does not fall below the critical limit.

One way of achieving this is to dilute the hydrolysis liquor to be introduced for example by installing a separator before the condenser 15, separately cooling the waste gas and returning the condensate accumulating to the preheater 13. Another way of ensuring that there is a sufficient quantity of water for evaporation in the preheater is to return a component stream of the output v to the preheater 13.

The process according to the invention can also be carried out using a suitable oxidation catalyst, optionally under more moderate reaction conditions. Solid catalysts can be separated off and recovered by subsequent filtration. Examples of suitable solid catalysts include active carbon and vanadium, molybdenum and tungsten oxides.

In order to oxidise the ingredients as completely as possible, molecular oxygen must be delivered to the wet-oxidation stage in at least stoichiometric quantities. Although an excess of oxygen provides for a higher conversion, it involves higher compression costs. In order completely to remove the organic secondary products accumulating in the hydrolysis liquor, the wet-oxidation stage can also be carried out with an incomplete conversion providing the stream of saponification liquor delivered to the wet-oxidation stage is increased to correspond to the lower conversion, i.e. providing the circulation of the streams $n$, $q$, $t$, $v$ (cf. FIG. 1) is accelerated. Any displacement which this may produce in the composition of the organic ingredients in the saponification stage does not have any negative effect upon the process according to the invention within certain limits.

The process according to the invention is illustrated by but by no means limited to the following Examples. Spent saponification liquors differing in their concentration taken from a continuous installation, in which cyclohexane is oxidised with atmospheric oxygen in the presence of metaboric acid to form a mixture of cyclohexanol and cyclohexanone by the process described above, and in which aqueous sodium hydroxide is used to saponify the reaction mixture, were used for the Examples.

Table 1

| Spent alkaline liquor No. | Composition of the alkaline liquors in % by weight | | |
|---|---|---|---|
| | 1 | 2 | 3 |
| Total alkali (expressed as NaOH) | 7.05 % | 7.12 % | 13.92 % |
| Free alkali (expressed as NaOH) | 1.30 % | 1.20 % | 1.89 % |
| Borate (expressed as $H_3BO_3$) | 1.79 % | 1.82 % | 0.98 % |
| Carbon | 6.25 % | 7.44 % | 17.0 % |
| Chemical oxygen demand (COD-value in mg of $O_2$/g) | 196 | 221 | 466 |

The alcohols and ketones recovered in accordance with the process of the invention can be used both in admixture and as individual substances after separation in a manner known per se for example as follows:

a. as solvents for lacquers
b. as the starting material for the production of dicarboxylic acids, e.g. adipic acid
c. as the starting material for the production of lactams, e.g. caprolactam.

EXAMPLES 1 to 4

Batch tests

An electrically heated two-liter fine-steel autoclave equipped with a magnetic lift stirrer, a gas inlet and reflux condenser was used as the test apparatus. Compressed air was used as the oxidation gas. The exhaust gas was removed through a valve behind the reflux condenser. The quantity of exhaust gas was measured by a rotameter. With the pressure-regulating valve for the compressed air open, the quantity of exhaust gas was regulated through the exhaust valve and, hence, the required quantity of compressed air indirectly regulated. 750 ml of alkali salt solution were introduced and heated to the required temperature with the exhaust valve closed. The test pressure was then adjusted through the compressed-air valve. The stirrer was adjusted to 50 strokes per minute. The test began with the opening of the exhaust valve and regulation of the required quantity of exhaust gas. Saponification liquor No. 1 was used.

The change in the COD-value from the initial value obtained under the test conditions gave the "conversion according to COD". Table 2 shows the test results, i.e. it was possible to reduce the COD-value by 83 to 99.4 %.

Table 2

| | Batch tests 1 – 4 | | | | |
|---|---|---|---|---|---|
| Test No. | Temp. °C | Pressure atms. | Waste gas Nl/h | Time h | Conversion according to COD % |
| 1 | 240 | 58 | 1500 | 4 | 83 |
| 2 | 270 | 90 | 1300 | 4 | 88 |
| 3 | 290 | 100 | 850 | 4 | 96 |
| 4 | 320 | 135 | 450 | 4 | 99.4 |

EXAMPLES 5 TO 10

Continuous tests

The arrangement used for tests 1 – 4 was additionally equipped with two submerged pipes. One was used to introduce the fresh saponification liquor through a metering pump, whilst the other, equipped with a descending condenser and valve, was used for releasing, cooling and venting the oxidised liquor. The waste gas was analysed for its $CO_2$, $CO$ and $O_2$ contents. The quantity of exhaust gas and, hence, indirectly the quantity of compressed air in these tests was measured in such a way that oxygen was available in a quantity of about 3 to 10 % more than that required for complete oxidation.

The tests were carried out as follows:

A certain quantity of liquor was introduced, the autoclave closed and compressed air introduced into it up to a pressure of 45 atms. The stirrer was then adjusted to 50 strokes per minute. After heating, the test pressure and quantity of exhaust gas were regulated and the liquor metering pump started up. Oxidised waste liquor was removed from the autoclave at a rate commensurate with that at which liquor was pumped in. After a test period of a few hours, the system was in a state of equilibrium, recognisable from constant analytical data of the waste-liquor samples. Table 3 shows the test data and results.

recognisable from constant analytical data of the discharge streams.

The test data and results are set out in Table 4. The analytical data of the organic phase discharged are of particular importance. If the organic phase is hydro- Table 3

| Test No. | Continuous tests 5 – 10 | | | | | | |
|---|---|---|---|---|---|---|---|
| | 5 | 6 | 7 | 8 | 9 | 10 | 11 |
| Alkaline liquor | No. 1 | 1 | 1 | 2 | 2 | 3 | 2 |
| Temperature °C | 270 | 290 | 290 | 290 | 310 | 290 | 330 |
| Pressure atms. | 100 | 100 | 100 | 100 | 125 | 100 | 161 |
| Quantity introduced (ml) | 1080 | 950 | 750 | 870 | 870 | 750 | 870 |
| Input (ml/h) | 500 | 500 | 1500 | 1500 | 1080 | 500 | 1500 |
| Input (g COD/h) | 107 | 107 | 320 | 365 | 263 | 274 | 365 |
| Residence time (h) | 2.15 | 1.9 | 0.5 | 0.58 | 0.8 | 1.5 | 0.58 |
| Quantity of exhaust gas (Nl/h) | 370 | 370 | 1100 | 1240 | 900 | 870 | 1240 |
| Conversion according to COD (%) | 85 | 90 | 85 | 86 | 93 | 74 | 94 |

EXAMPLE 12

Recirculation of wet-oxidised alkaline liquor

Organic reaction mixture from the cyclohexane oxidation system described above, from which most of the boric acid had been removed by extraction with water, was saponified with a alkaline solution purified by wet oxidation in accordance with test 10.

The organic phase and liquor were preheated to the required saponification temperature and introduced into a vigrously stirred 500 ml glass flask. Saponification took place in this flask over a residence time of about 5.3 minutes at a temperature of 72°C. The mixture was pumped into a separation vessel operated at a temperature of around 68°C. The organic phase ran off freely from the separation vessel through an overflow. The aqueous phase was pumped back to the mixing vessel by means of a liquor recirculation pump, producing an inner aqueous circuit (circulation 550 gh). The spent saponification liquor was discharged under level control behind the liquor recirculation pump. After a few hours, the system was in a state of equilibrium, lysed a second time with 10 % sodium hydroxide, its acid number and saponification number are further reduced, although no more cyclohexanol is liberated. On the other hand, acid number and saponification number can also be further reduced by increasing the residence time, although once again the yield remains the same. Comparison with conventional saponification carried out on a large scale with dilute sodium hydroxide at the same temperature and over the same residence time (cf. last column of Table 4) confirms that following elimination of the organic impurities by wet oxidation the saponification liquor can be recycled and reused without any adverse effects upon the yield of ketone/alcohol mixture.

Table 4

Saponification with wet oxidixed saponification liquor at 72°C (% = % by weight)

| | Input | | Output (test) | | | Output (large scale working) organic phase |
|---|---|---|---|---|---|---|
| | organic phase | liquor | organic phase untreated | after-saponified | liquor | |
| Quantity (g/h) | 4000 | 192 | approx. 3900 | | 240 | |
| cyclohexanol + cyclohexanone 1) | 10.55 % | — | 11.10 % | 11.09 % | — | 11.10 % |
| acid number 2) | 27 | | 3.5 | 0.2 | | 0 |
| saponification number 2) | 47 | | 14.6 | 6.4 | | 10 |
| total alkali 3) | | 13.8 % | | | 11.1 % | |
| free alkali 3) | | 9.7 % | | | 4.1 % | |
| COD (mg of O₂/g) | | 83 | | | 253 | |
| carbon (organically combined) | | 2.29 % | | | 6.60 % | |

1)determined by gas chromatography; average values from 3 to 5 measurements
2)in mg of KOH/g of cyclohexanol/cyclohexanone mixture
3)expressed as NaOH The organic phase accumulating during this test readily lent itself to working up by distillation into a cyclohexanol/cyclohexanone mixture equal in quality to the mixture obtained on a large scale by the conventional process.

The spent alkaline liquor from this test (for composition see penultimate column of Table 4) was subjected to continuous wet-oxidation for about 40 minutes at 290°C/100 atms. in a test autoclave (for description see tests 5 to 11). The conversion, based on the COD-value, amounted to 87 %.

The residence times quoted in the tests are essentially governed by the parameters of the test apparatus and can be shortened by suitable techanical measures.

What is claimed is:

1. In a process for the oxidation of hydrocarbons to form alcohol-ketone mixtures which comprises:
   a. reacting a hydrocarbon having from 4 to 20 carbon atoms with a gas containing molecular oxygen in the presence of an oxidation catalyst;
   b. washing the reaction mixture from (a) in an intermediate hydrolysis stage with water and separating said catalyst, leaving a washed organic reaction mixture;
   c. saponifying the organic reaction mixture from (b) with an aqueous alkaline solution and separating the organic phase from the aqueous alkaline phase that forms;
   d. recovering said alcohol-ketone mixture from the organic phase from (c);
   e. recovering alcohols and the other secondary products in the aqueous alkaline phase from (c) by distallation or stripping;
   the improvement which comprises:
   f. subjecting the aqueous alkaline phase from (e) which contains organic impurities to a liquid phase oxidation with a gas containing molecular oxygen in at least a stoichiometric quantity sufficient to completely burn the organic impurities and to form carbon dioxide water and an alkali carbonate/bicarbonate solution, said oxidation taking place in a reaction zone heated to at least 200°C and under a pressure sufficient to keep at least some of the water in the liquid phase; and
   g. returning said alkali carbonate/bicarbonate solution to saponification step (c).

2. Process of claim 1 wherein the liquid-phase oxidation is carried out at a temperature of from 200° to 370°C under a pressure of from 20 to 220 atms.

3. Process of claim 2 werein the liquid-phase oxidation is carried out at a temperature of from 270° to 350° under a pressure of from 60 to 200 atms.

4. Process of claim 2 wherein liquid-phase oxidation of the alkaline solutin is carried out continuously.

5. Process of claim 2 wherein the hydrocarbon is cyclohexane or cyclododecane.

6. In a process for the oxidation of hydrocarbons to form alcohol-ketone mixtures which comprises:
   a. reacting a hydrocarbon having from 4 to 20 carbon atoms with a gas containing molecular oxygen in the presence of a boron compound;
   b. washing the reaction mixture from (a) in an intermediate hydrolysis stage with water and separating said boron compound, leaving a washed organic reaction mixture;
   c. saponifying the organic reaction mixture from (b) with an aqueous alkaline solution and separating the organic phase from the aqueous alkaline phase that forms;
   d. recovering said alcohol-ketone mixture from the organic phase from (c);
   e. recovering alcohols and the other secondary products in the aqueous alkaline phase from (c) by distillation or stripping;
   the improvement which comprises:
   f. subjecting the aqueous alkaline phase from (e) which contains organic impurities to a liquid phase oxidation with a gas containing molecular oxygen in at least a stoichiometric quantity sufficient to completely burn the organic impurities and to form carbon dioxide water and an alkali carbonate/bicarbonate solution, said oxidation taking place in a reaction zone heated to at least 200°C and under a pressure sufficient to keep at least some of the water in the liquid phase; and
   g. returning said alkali carbonate/bicarbonate solution t saponification step (c).

7. Process of claim 6 wherein the liquid-phase oxidation is carried out at a temperature of from 200° to 370°C under a pressure of from 20 to 220 atms.

8. Process of claim 7 wherein the liquid-phase oxidation is carried out at a temperature of from 270° to 350°C under a pressure of from 60 to 200 atms.

9. Process of claim 6 wherein liquid-phase oxidation of the alkaline solution is carried out continuously.

10. Process of claim 6 wherein the hydrocarbon is cyclohexane or cyclododecane.

11. In a process for the oxidation of hydrocarbons to form alcohol-ketone mixtures which comprises:
    a. reacting a hydrocarbon having from 4 to 20 carbon atoms with a gas containing molecular oxygen in the presence of an oxidation catalyst and a boron compound;
    b. washing the reaction mixture from (a) in an intermediate hydrolysis stage with water and separating said catalyst and boron compound, leaving a washed organic reaction mixture;
    c. saponifying the organic reaction mixture from (b) with an aqueous alkaline solution and separating the organic phase from the aqueous alkaline phase that forms;
    d. recovering said alcohol-ketone mixture from the organic phase from (c);
    e. recovering alcohols and the other secondary products in the aqueous alkaline phase from (c) by distillation or stripping;
    the improvement which comprises:
    f. subjecting the aqueous alkaline phase from (e) which contains organic impurities to a liquid phase oxidation with a gas containing molecular oxygen in at least a stoichiometric quantity sufficient to completely burn the organic impurities and to form carbon dioxide water and an alkali carbonate/bicarbonate solution, said oxidation taking place in a reaction zone heated to at least 200°C and under a pressure sufficient to keep at least some of the water in the liquid phase; and
    g. returning said alkali carbonate/bicarbonate solution to saponification step (c).

12. Process of claim 11 wherein the liquid-phase oxidation is carried out at a temperature of from 200° to 370°C under a pressure of from 20 to 220 atms.

13. Process of claim 12 wherein the liquid-phase oxidation is carried out at a temperature of from 270° to 350°C under a pressure of from 60 to 200 atms.

14. Process of claim 11 wherein liquid-phase oxidation of the alkaline solution is carried out continuously.

15. Process of claim 11 wherein the hydrocarbon is cyclohexane or cyclododecane.

* * * * *

UNITED STATES PATENT AND TRADEMARK OFFICE
CERTIFICATE OF CORRECTION

PATENT NO. : 3,946,077
DATED : March 23, 1976
INVENTOR(S) : Reinhard Thiel

It is certified that error appears in the above--identified patent and that said Letters Patent are hereby corrected as shown below:

| Column | Line | |
|---|---|---|
| 1 | 24 | Add "h" to "te". |
| 1 | 34 | "metabroic" should be spelled --metaboric--. |
| 2 | 22 | "assumulates" should be spelled "accumulates". |
| 2 | 26,36 | Delete "hydrolysis" and in its place insert -saponification--. |
| 4 | 18 | "safonification" should be spelled "saponification". |
| 10 | 12 | Add the "o" to "t" to spell "to". |

Signed and Sealed this

Sixth Day of July 1976

[SEAL]

Attest:

RUTH C. MASON
*Attesting Officer*

C. MARSHALL DANN
*Commissioner of Patents and Trademarks*